US009265483B2

(12) United States Patent
Borden et al.

(10) Patent No.: US 9,265,483 B2
(45) Date of Patent: Feb. 23, 2016

(54) MEDICAL IMAGING CONTRAST DEVICES, METHODS, AND SYSTEMS

(75) Inventors: Mark A. Borden, Boulder, CO (US); Jameel A. Feshitan, New York, NY (US); Elisa E. Konofagou, New York, NY (US); Fotios Vlachos, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 216 days.

(21) Appl. No.: 13/814,623

(22) PCT Filed: Aug. 5, 2011

(86) PCT No.: PCT/US2011/046865
§ 371 (c)(1),
(2), (4) Date: May 31, 2013

(87) PCT Pub. No.: WO2012/019172
PCT Pub. Date: Feb. 9, 2012

(65) Prior Publication Data
US 2013/0289398 A1 Oct. 31, 2013

Related U.S. Application Data

(60) Provisional application No. 61/371,647, filed on Aug. 6, 2010, provisional application No. 61/371,982, filed on Aug. 9, 2010.

(51) Int. Cl.
| | | |
|---|---|---|
| A61B 8/08 | (2006.01) | |
| A61K 49/18 | (2006.01) | |
| A61K 49/22 | (2006.01) | |
| A61N 7/02 | (2006.01) | |

(Continued)

(52) U.S. Cl.
CPC .............. *A61B 8/481* (2013.01); *A61K 49/1809* (2013.01); *A61K 49/222* (2013.01); *A61N 7/02* (2013.01); *A61B 2019/5236* (2013.01); *A61N 2007/0039* (2013.01)

(58) Field of Classification Search
CPC ........... A61B 8/481; A61B 2019/5236; A61K 49/1809; A61K 49/222; A61N 2007/0039; A61N 7/02
See application file for complete search history.

(56) References Cited

U.S. PATENT DOCUMENTS

| | | |
|---|---|---|
| 3,598,111 A | 8/1971 | Kahn et al. |
| 4,777,599 A | 10/1988 | Dorogi et al. |

(Continued)

FOREIGN PATENT DOCUMENTS

| | | |
|---|---|---|
| WO | WO 2010044385 | 4/2010 |
| WO | WO 2010063951 | 6/2010 |

OTHER PUBLICATIONS

International Search Report and Written Opinion for International Application No. PCT/US11/46865.

(Continued)

*Primary Examiner* — Michael Rozanski
(74) *Attorney, Agent, or Firm* — Miles & Stockbridge, PC; Mark A. Catan

(57) ABSTRACT

Systems, methods, and devices for generating and using size-selected lanthanide-coated microbubbles for controlling an imaging signal via microbubble fragmentation and for magnetic resonance imaging guided focused ultrasound therapy.

21 Claims, 7 Drawing Sheets

Schematic of separation by centrifugation

(51) Int. Cl.
*A61B 19/00* (2006.01)
*A61N 7/00* (2006.01)

(56) References Cited

U.S. PATENT DOCUMENTS

| | | | |
|---|---|---|---|
| 5,107,837 | A | 4/1992 | Ophir et al. |
| 5,178,147 | A | 1/1993 | Ophir et al. |
| 5,309,914 | A | 5/1994 | Iinuma |
| 5,406,950 | A | 4/1995 | Brandenburger et al. |
| 5,435,310 | A | 7/1995 | Sheehan et al. |
| 5,601,084 | A | 2/1997 | Sheehan et al. |
| 5,606,971 | A | 3/1997 | Sarvazyan |
| 5,662,113 | A | 9/1997 | Liu |
| 5,722,411 | A | 3/1998 | Suzuki et al. |
| 5,810,731 | A | 9/1998 | Sarvazyan et al. |
| 5,840,028 | A | 11/1998 | Chubachi et al. |
| 5,928,151 | A | 7/1999 | Hossack et al. |
| 6,102,864 | A | 8/2000 | Hatfield et al. |
| 6,102,865 | A | 8/2000 | Hossack et al. |
| 6,123,669 | A | 9/2000 | Kanda |
| 6,241,675 | B1 | 6/2001 | Smith et al. |
| 6,246,895 | B1 | 6/2001 | Plewes |
| 6,312,382 | B1 | 11/2001 | Mucci et al. |
| 6,352,507 | B1 | 3/2002 | Torp et al. |
| 6,485,705 | B1 | 11/2002 | Schneider et al. |
| 6,508,768 | B1 | 1/2003 | Hall et al. |
| 6,537,217 | B1 | 3/2003 | Bjærum et al. |
| 6,537,221 | B2 | 3/2003 | Criton et al. |
| 6,671,541 | B2 | 12/2003 | Bishop et al. |
| 6,683,454 | B2 | 1/2004 | Rehwald et al. |
| 6,685,641 | B2 | 2/2004 | Liu |
| 6,875,176 | B2 | 4/2005 | Mourad et al. |
| 7,055,378 | B2 | 6/2006 | Su et al. |
| 7,257,244 | B2 | 8/2007 | Miga |
| 7,331,926 | B2 | 2/2008 | Varghese et al. |
| 7,421,101 | B2 | 9/2008 | Georgescu et al. |
| 7,601,122 | B2 | 10/2009 | Zagzebski et al. |
| 7,753,847 | B2 | 7/2010 | Greenleaf et al. |
| 8,029,444 | B2 | 10/2011 | Pedrizzetti et al. |
| 2002/0065461 | A1 | 5/2002 | Cosman |
| 2003/0220556 | A1 | 11/2003 | Porat et al. |
| 2004/0006266 | A1 | 1/2004 | Ustuner et al. |
| 2004/0059224 | A1 | 3/2004 | Varghese et al. |
| 2004/0092816 | A1 | 5/2004 | Ossmann et al. |
| 2004/0249580 | A1 | 12/2004 | Pourcelot et al. |
| 2005/0004466 | A1 | 1/2005 | Hynynen et al. |
| 2005/0054930 | A1 | 3/2005 | Rickets et al. |
| 2005/0059876 | A1 | 3/2005 | Krishnan et al. |
| 2005/0080336 | A1 | 4/2005 | Byrd et al. |
| 2005/0201942 | A1 | 9/2005 | Dugstad et al. |
| 2005/0267695 | A1 | 12/2005 | German |
| 2006/0058673 | A1 | 3/2006 | Aase et al. |
| 2006/0074315 | A1 | 4/2006 | Liang et al. |
| 2006/0173320 | A1 | 8/2006 | Radulescu |
| 2007/0049824 | A1 | 3/2007 | Konofagou et al. |
| 2007/0081946 | A1 | 4/2007 | Schneider et al. |
| 2007/0219447 | A1 | 9/2007 | Kanai et al. |
| 2007/0276242 | A1 | 11/2007 | Konofagou |
| 2007/0276245 | A1 | 11/2007 | Konofagou |
| 2008/0145311 | A1 | 6/2008 | Lanza et al. |
| 2008/0194957 | A1 | 8/2008 | Hoctor et al. |
| 2008/0206131 | A1 | 8/2008 | Jaffray et al. |
| 2008/0269606 | A1 | 10/2008 | Matsumura |
| 2008/0285819 | A1 | 11/2008 | Konofagou et al. |
| 2010/0158815 | A1 | 6/2010 | Wang et al. |
| 2011/0044903 | A1 | 2/2011 | Borrelli |
| 2011/0208038 | A1 | 8/2011 | Konofagou et al. |

OTHER PUBLICATIONS

Feshitan et al., "Magnetic Resonance Properties of Gd(III)-Bound Lipid-Coated Microbubbles and their Cavitation Fragments", Langmuir, 2012, vol. 28, pp. 15336-15343.

Feshitan et al., "Theranostic Gd(III)-lipid mcirobubbles for MRI-guided focused ultrasound surgery", Biomaterials, 2012, vol. 33, pp. 247-255.

Duck, "Physical properties of tissue: a comprehensive reference book. 1990 Academic Press," London, UK.

Jensen et al., "Calculation of pressure fields from arbitrarily shaped, apodized, and excited ultrasound transducers," IEEE Transactions on Ultrasonics, Ferroelectrics and Frequency Control, vol. 39(2), pp. 262-267, Mar. 1992.

Mitri et al., "Chirp imaging vibro-acoustography for removing the ultrasound standing wave artifact," IEEE transactions on medical imaging, vol. 24(10), pp. 1249-1255, Oct. 2005.

Bers, "Cardiac excitation-contraction coupling", Nature, Jan. 10, 2002, vol. 415:198-205.

Ramanathan et al., (2004) "Noninvasive electrocardiographic imaging for cardiac electrophysiology and arrhythmia," Nat Med 10(4):422-428.

Berger et al., (2006) "Single-Beat Noninvasive Imaging of Cardiac Electrophysiology of Ventricular Pre-Excitation. Journal of the American College of Cardiology," 48(10):2045-2052.

Greenstein et al., (2006) "Mechanisms of Excitation-Contraction Coupling in an Integrative Model of the Cardiac Ventricular Myocyte," Biophysical Journal 90:77-91.

Rice et al., "Approximate model of cooperative activation and crossbridge cycling in cardiac muscle using ordinary differential equations," Biophys. J 95:2368-2390, Sep. 2008.

Campbell et al., "Mechanisms of transmurally varying myocyte electromechanics in an integrated computational model," Phl. Trans. R. Soc. A., 366:3361-3380, Jul. 1, 2008.

Gurev et al., "Distribution of Electromechanical Delay in the Heart: Insights from a Three-Dimensional Electromechanical Model," Biophysical Journal 99:745-754, Aug. 2010.

Badke et al., (1980) "Effects of ventricular pacing on regional left ventricular performance in the dog," Am J Physiol Heart Circ Physiol 238:H858-867.

Wyman et al., (1999) "Mapping propagation of mechanical activation in the paced heart with MRI tagging," Am J Physiol Heart Circ Physiol 276:H881-891.

Prinzen et al., (1992) "The time sequence of electrical and mechanical activation during spontaneous beating and ectopic stimulation," Eur Heart J 13:535-543.

Provost et al., (2010) "Electromechanical Wave Imaging of Normal and Ischemic Hearts in Vivo," IEEE Trans. Med. Imaging 29(3):625-635.

Shehata et al., (2009) "Myocardial tissue tagging with cardiovascular magnetic resonance," Journal of Cardiovascular Magnetic Resonance 11:55.

Pernot et al., (2007) "ECG-gated, Mechanical and Electromechanical Wave Imaging of Cardiovascular Tissues In Vivo," Ultrasound in Medicine & Biology 33(7):1075-1085.

Provost et al., (2008) in 2008 IEEE International Ultrasonics Symposium (Beijing, China).

Durrer et al. (1970) "Total Excitation of the Isolated Human Heart. Circulation," 41:899-912.

Sengupta et al., (2008) "Electromechanical activation sequence in normal heart," Heart Fail Clin. 4:303-14.

Scher et al., (1956) "The pathway of ventricular depolarization in the dog," Circ. Res 4:461-469.

Faris et al., (2003) "Novel Technique for Cardiac Electromechanical Mapping with Magnetic Resonance Imaging Tagging and an Epicardial Electrode Sock," Ann Biomed Eng. 31:430-440.

Gurev et al., (2009) "In silico characterization of ventricular activation pattern by electromechanical wave imaging," Supplement to Heart Rhythm 6:S357.

Ramanathan et al., "Activation and repolarization of the normal human heart under complete physiological conditions," Proceedings of the National Academy of Sciences 103(16):6309-6314, Apr. 18, 2006.

Lee et al., "Theoretical Quality Assessment of Myocardial Elastography with In Vivo Validation," Ultrasonics, Ferroelectrics and Frequency Control, IEEE Transactions on 54(1):2233-2245, Nov. 11, 2007.

Kimber et al., (1996) "A Comparison of Unipolar and Bipolar Electrodes During Cardiac Mapping Studies," Pacing Clin Electro 19:1196-1204.

(56) References Cited

OTHER PUBLICATIONS

Kallel et al., (1997) "A least-squares strain estimator for elastography," Ultrason Imaging 19:195-208.
Luo et al., "High-frame rate, full-view myocardial elastography with automated contour tracking in murine left ventricles in vivo," IEEE Transactions on Ultrasonics, Ferroelectrics and Frequency Control, 55(1):240-248, Jan. 2008.
Lai et al., (1993) "Introduction to Continuum Mechanics," (Pergamon Pr). 3rd Ed., Contents.
Stewart et al., "Blood-eye barriers in the rat: Correlation of ultrastructure with function," J. Comp. Neurol., vol. 340, No. 4, pp. 566-576, 1994.
Samuel et al., "An ex vivo study of the correlation between acoustic emission and microvascular damage," Ultrasound Med. Biol., vol. 35, No. 9, pp. 1574-1586, 2009.
Luo et al., "Pulse wave imaging of normal and aneurysmal abdominal aortas in vivo", IEEE Trans. Med. Imaging 28(4): 477-486, 2009.
Luo et al., "A fast normalized cross-correlation method for motion estimation," IEEE Trans. Ultrason. Ferroelectr. Control 57(6): 1347-1357, Jun. 2010.
Maleke et al., "Single-Element focused Ultrasound Transducer Method for Harmonic Motion Imaging," Ultrason. Imagin, vol. 28, No. 3, pp. 144-158, 2006.
Maleke et al., "In Vivo Feasibility of Real-time Monitoring of Focused Ultrasound Surgery (FUS) Using Harmonic Motion Imaging (HMI)," IEEE Trans. Biomed. Eng., vol. 57(1), pp. 7-11, Jan. 2010.
Vappou et al., "Quantitative Viscoelastic Parameters Measured by Harmonic Motion Imaging," Phys. Med. Biol., vol. 54, pp. 3579-3595, Mar. 2009.
Ophir et al., "Elastography: A quantitative method for imaging the elasticity of biological tissues," Ultrasonic Imaging, vol. 13(2), pp. 111-134, 1991.
Huang et al., "Watershed Segmentation for Breast Tumor in 2-D Sonography," May 2004, Ultrasound in Medicine and Biology, pp. 625-632.
Chang et al., "3-D US Frame Positioning Using Speckle Decorrelation and Image Registration," Jun. 2003, Ultrasound in Medicine and Biology, pp. 801-812.
Luo et al., "Myocardial elastography at both high temporal and spatial resolution for the detection of infarcts," Ultrasound in Med. & Bio, vol. 33(8), pp. 1206-1223, Aug. 2007.
Wang et al., "A composite high frame-rate system for clinical cardiovascular imaging," IEEE Transactions on Ultrasonics, Ferroelectrics, and Frequency Control, vol. 55(10), pp. 2221-2233, Oct. 2008.
Wang et al., "A composite imaging technique for high frame-rate and full-view cardiovascular ultrasound and elasticity imaging," IEEE International Ultrasonics Symposium, New York, NY, Oct. 28-31, 2007.
Kanai, "Propagations of spontaneously actuated pulsive vibration in human heart wall and in vivo viscoelasticity estimation," IEE Transaction on Ultrasonics, Ferroelectrics, and Frequency Control, vol. 52(11), pp. 1931-1942, Nov. 2005.
Bercoff et al., "Supersonic Shear Imaging: A new technique for soft tissue elasticity mapping," IEEE Transactions on Ultrasonics, Ferroelectrics, and Frequency Control, vol. 51(4), pp. 396-409, Apr. 2004.
McLaughlin et al., "Piezoelectric sensor determination of arterial pulse wave velocity," Physiol. Meas., vol. 24(3), pp. 693-702, 2003.
Greenwald, "Pulse pressure and arterial elasticity," QJM: An International Journal of Medicine, vol. 95(2), pp. 107-112, 2002.
Kanai et al., "Myocardial rapid velocity distribution," Ultrasound Med. & Biol., vol. 27(4), pp. 481-498, Apr. 2001.
Rogers et al., "Age-associated changes in regional aortic pulse wave velocity," J Am Coll. Cardiol., vol. 38(4), pp. 1123-1129, 2001.
Declerck et al., "Left ventricular motion reconstruction from planar tagged MR images: a comparison," Phys. Med. Biol., vol. 45(6), pp. 1611-1632, Jun. 2000.
Kanai et al., "Transcutaneous measurement of frequency dispersion in the regional pulse wave velocity," IEEE Ultrasonics Symposium, 2000.
Sinkus et al., "High-resolution tensor MR elastography for breast tumor reduction," Phys Med Biol, 2000, 45(6): 1649-1664.
Roth, "Influence of a perfusing bath on the foot of the cardiac action potential," Circulation Research, vol. 86, E19-E22, 2000.
Wang et al., "Increased aortic stiffness assessed by pulse wave velocity in apolipoprotein E-deficient mice," Am J Physiol Heart Circ. Physiol., vol. 278, No. 2, pp. H428-H434, 2000.
Sandrin et al., "Time-resolved pulsed elastography with ultrafast ultrasonic imaging," Ultrason Imaging, vol. 21(4), pp. 259-272, 1999.
Cutnell et al., Physics, Fourth Edition, New York. Table of Contents, 1998.
Heimdal et al., "Real-time strain rate imaging of the left ventricle by ultrasound," J Am Soc. Echocardiog., vol. 11(11), pp. 1013-1019, 1998.
Konofagou et al., "A New Elastographic Method for Estimation and Imaging od Lateral Strains, Corrected Axial Strains and Poison's Ratios in Tissues," Ultrasound in Medicine & Biology 24(8): 1183-1199, 1998.
Konofagou et al., "Three-dimensional Motion estimation in Elastography," IEEE Proceedings of the Symposium of Ultrasonics, Ferroelectrics, and Frequency Control in Sendai Japan, pp. 1745-1748, vol. 2, 1998.
Nichols et al., "Vascular Impedance. In McDonald's: blood flow in arteries: theoretical, experimental, and clinical principles," E Arnold, London, 1998. Table of Contents.
Sarvazyan et al., "Shear wave elasticity imaging: A new ultrasonic technology of medical diagnostics," Ultrasound Med Biol, vol. 24(9), pp. 1419-1435, Nov. 1998.
Spach et al., "Extracellular discontinuities in cardiac muscle—Evidence for capillary effects on the action potential foot," Circulation Research, vol. 83, pp. 1144-1164, 1998.
Sutherland, "Color Doppler Myocardial Imaging—Potential Applications in Acquired and Congenitial Heart Disease," Acta Paediatr, 84: pp. 40-48, Aug. 1995.
Walker et al., "A Fundamental Limit on Delay Estimation Using Partially Correlated Speckle Signals," IEEE T Ultrason Ferr, vol. 42(2), pp. 301-308, Mar. 1995.
Gupta, et al., "Changes in Passive mechanical Stiffness of Myocardial Tissue with Aneurysm Formation," Circulation, vol. 89, pp. 2315-2326, 1994.
Fung, "Biomechanics—Mechanical Properties of Living Tissues," New York, 1993, Table of Contents.
Kanai, et al., "A New Method for Measuring Small Local Vibrations in the Heart Using Ultrasound," IEEE T Bio-Med Eng, vol. 40(12), pp. 1233-1242, Dec. 1993.
Zerhouni, et al., "Human Heart: tagging with MR imaging—a method for noninvasive assessment of myocardial motion," Radiology 169(1): 59-63, Oct. 1988.
Bonnefous, et al., "Time domain formulation of pulse-Doppler ultrasound and blood velocity estimation by cross-correlation," Ultrason Imaging, vol. 8(2), pp. 73-85, Apr. 1986.
Avolio, et al., "Effects of aging on changing arterial compliance and left ventricular load in a northern Chinese urban community," Circulation, vol. 68(1), pp. 50-58, 1983.
Edwards, et al., "Effects of lschemia on Left-Ventricular Regional Function in the Conscious Dog," American Journal of Physiology, vol. 240, pp. H413-H420, 1981.
Henderson, et al., "Series Elasticity of Heart Muscle During Hypoxia," Cardiovascular Research, vol. 5, pp. 10-14, 1971.
Konofagou et al., "Myocardial Elastography—Feasibility Study in Vivo," Ultrasound Med & Biol, vol. 28(4), pp. 475-482, Apr. 2002.
McNally et al., "Computer Vision Elastography: Speckle Adaptive Motion Estimation for Elastography Using Ultrasound Sequences." IEEE Transactions on Medical Imaging, vol. 24, No. 6, pp. 755-766 (2005).
Zheng, et al., "High Resolution ultrasound elastomicroscopy imaging of soft tissues: system development and feasibility; Ultrasound elastomicroscopy," Physics in Medicine and Biology, vol. 49, No. 17, pp. 3925-3938 (Sep. 7, 2004).

(56) References Cited

OTHER PUBLICATIONS

Chen et al., "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Konofagou et al., "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Qin et al., "The Natural Frequency of Nonlinear Oscillation of Ultrasound Contrast Agents in Microvessels," Ultrasound in Med. & Biol., vol. 33, No. 7, pp. 1140-1148, 2007.
Konofagou et al., "Noninvasive Electromechanical Wave Imaging and Conduction Velocity Estimation In Vivo," Ultrasonics Symposium, 2007 IEEE, pp. 969-972, 2007.
Konofagou et al., "Electromechanical Wave imaging for noninvasive mapping of the 3D electrical activation sequence in canines and humans in vivo," Journal of Biomechanics, 45(5):856-864 (Mar. 15, 2012).
Otani et al., "Transmural ultrasound-based visualization of patterns of action potential wave propagation in cardiac tissue," Annals Biomedical Engineering, 38(10):3112-3123 (2010).
Chen et al., "Architectural Acoustics and Noise: Advancements and Best Practices in Instrumentation for Architectural Acoustics and Noise, J. Acoust. Soc. Am.; 164th Meeting: Acoustical Society of America, 132(3, Pt. 2):1977-2018 (Sep. 2012) Cited in IR Assessments: Chen, et al., Radiation-Force-Based Estimation of Acoustic Attenuation Using Harmonic Motion Imaging (HMI) in Phantoms and In Vitro Livers Before and After HIFU Ablation", Ultrasound in Medicine and Biology, Submitted and included in IR Report.
Chen et al., "Engineering Acoustics and ASA Committee on Standards: Sound Intensity Measurements, J. Acoust. Soc. Am.; 164th Meeting: Acoustical Society of America, 132(3, Pt. 2):1984 (Sep. 2012); Cited in IR Assessment as: Chen, et al., Radiation-Force-Based Estimation of Acoustic Attenuation Using Harmonic Motion Imaging (HMI) in Phantoms and In Vitro Livers Before and After HIFU Ablation", Ultrasound in Medicine and Biology, Submitted and included in IR Report.
Palmeri et al., "Characterizing Acoustic Attenuation of Homogeneous Media Using Focused Impulsive Acoustic Radiation Force," Ultrasonic Imaging, 28(2):114-128 (2006).
Duerinckx et al., "In vivo Acoustic Attenuation in Liver: Correlations with Blood Tests and Histology," Ultrasonic in Medicine & Biology, 14(5):405-413 (1988).
Fujii et al., "A New Method for Attenuation Coefficient Measurement in the Liver," Journal of Ultrasound in Medicine, 21(7):783-788 (2002).
Damianou et al., "Dependence of Ultrasonic Attenuation and absorption in dog soft tissues on Temperature and Thermal dose," The Journal of Acoustical Society of America, 102(1):628-634 (1997).
Techavipoo et al., "Temperature Dependence of Ultrasonic Propagation Speed and Attenuation in Excised Canine Liver Tissue Measured Using Transmitted and Reflected Pulses," The Journal of Acoustical Society of America, 115(6):2859-2865 (2004).
Papadakis, "Ultrasonic Instruments & Devices," Academic Press, 1999.
Cobbold, "Foundations of biomedical ultrasound," Biomedical engineering series, Oxford University Press, pp. 422-423 (2006).
Jasaityte et al., "Current state of three dimensional myocardial strain estimation using echocardiography," Journal of the American Society of Echocardiography, 26(1):15-28 (2013).

Konofagou et al., "Noninvasive electromechanical wave imaging and conduction-relevant velocity estimation in vivo," Ultrasonics, 50(2):208-215 (2010).
Provost et al., "Imaging the electromechanical activity of the heart in vivo," Proceedings of the National Academy of Sciences, 108:8565-8570 (2011).
Provost et al., "Mapping of cardiac electrical activation with electromechanical wave imaging: An in silico-in vivo reciprocity study," Heart Rhythm, 8(5):752-759 (2011).
Otani et al., "Use of ultrasound imaging to map propagating action potential waves in the heart," Computers in Cardiology, 36:617-620 (2009).
Ginat et al., "High-resolution ultrasound elastography of articular cartilage in vitro," Proceedings of the 28th IEEE EMBS Annual International Conference, New York City, USApp. 6644-6647 (Aug. 30-Sep. 3, 2006).
Zheng et al., "Ultrasonic measurement of depth-dependent transient behaviors of articular cartilage under compression," Journal of Biomechanics, 38:1830-1837 (2005).
Shinna et al., "Realtime tissue elasticity imaging using the combined autocorrelation method," J. Med. Ultrasonics, 29(autumn):119-128 (2002).
Borden et al., "Ultrasound Radiation Force Modulates Ligand Availability on Target Contrast Agents," Mol. Imaging, 5:139-147 (2006).
Vial (en.wikipedia.org/wiki/Vial) downloaded May 20, 2014.
European Search Report for EP Application No. EP 10838238, dated May 6, 2014.
International Search Report for PCT/US2011/34704.
Zwanenburg et al., (2004) "Timing of cardiac contraction in humans mapped by high-temporal-resolution MRI tagging: early onset and late peak of shortening in lateral wall," Am J Physiol Heart Circ Physiol 286:H1872-1880.
Walker et al., (1994) "A fundamental limit on the performance of correlation based phase correction and flow estimation techniques," Ultrasonics, Ferroelectrics and Frequency Control, IEEE Transactions on 41(5):644-654, Sep. 1994.
Pernot et al., "Electromechanical Imaging of the Myocardium at Normal and Pathological States", Ultrasonics Symposium, 2005 IEEE, pp. 1091-1094, 2005.
Fenster et al., "Three-dimensional ultrasound imaging," Physics in Medicine and Biology, 46(5):R67-R99 (2001).
De Craene et al., "Temporal diffeomorphic free-form deformation: Application to motion and strain estimation from 3D echocardiography," Medical Image Analysis, 16(2):427-450 (2012).
Housden et al., "Ultrasonic imaging of 3D displacement vectors using a simulated 2D array and beamsteering," Ultrasonics, 53(2):615-621 (2013).
DuBose et al., "Confusion and Direction in Diagnostic Doppler Sonography," Journal of Diagnostic Medical Sonography, 25(3):173-177 (2009).
Yuh, et. al., "Delivery of Systemic Chemotherapeutic Agent to Tumors by Using Focused Ultrasound: Study in a Murine Model," Radiology, 234(2): 431-437, 2005.
Tanter et al., "Ultrafast compound imaging for 2-D motion vector estimation: application to transient elastography," IEEE Trans Ultrason Ferroelectr Freq Control, vol. 49(10), pp. 1363-1374, 2002.
Brooks et al., "Electrical Imaging of the Heart," IEEE Signal Processing Magazine, vol. 14(1), pp. 24-42, Jan. 1997.
Luo et al., "Myocardial elastography at both high temporal and spatial resolution for the detection of infarcts," Ultrasound Med. Biol. 33(8): 1206-1223, 2007.

MEDICAL IMAGING CONTRAST DEVICES, METHODS, AND SYSTEMS

CROSS-REFERENCE TO RELATED APPLICATIONS

This application is a national stage application of International Application No. PCT/US11/46865, filed Aug. 5, 2011, which claims priority to and the benefit of U.S. Provisional Application Nos. 61/371,647, filed on Aug. 6, 2010, and 61/371,982, filed on Aug. 9, 2010, the contents of which are incorporated herein by reference in their entireties.

STATEMENT REGARDING FEDERALLY SPONSORED RESEARCH

This invention was made with government support under Grant No. RO1 EB9041 awarded by National Institute of Health. The government has certain rights in this invention.

FIELD

The present disclosure is directed to medical imaging contrast devices, systems, and methods, and, more particularly to methods, systems, and devices for medical imaging contrast using lanthanide-coated microbubbles and methods, systems, and devices for magnetic resonance imaging guided focused ultrasound therapy (MRIg-FUS).

SUMMARY

A paramagnetic lanthanide ion, such as gadolinium ($Gd^{3+}$), can be loaded through chelation to a macrocyclic molecule onto a lipid shell of a microbubble. The intrinsic gas/liquid interface of the microbubble can cause a local inhomogeneity in the magnetic field. This inhomogeneity can induce a magnetic susceptibility difference, which can be used to generate a negative contrast in a magnetic resonance image (MRI) where the image is weighted by longitudinal relaxation (R1). When the microbubble is intact with a gas core (and therefore a gas/liquid interface) the contrast enhancement may be minimal. However, when the microbubble is fragmented and the gas core is dissolved, the fragmented shell of the microbubble that is left behind can create a positive contrast in the image weighted by R1. Thus, the lanthanide-coated microbubble can allow detection of the location and intensity of ultrasound-induced microbubble destruction, for example, during MRI-guided ultrasound therapies, such as MRI-guided high-intensity focused ultrasound therapies. Monitoring of such therapies can thereby be improved while reducing negative side effects.

DETAILED DESCRIPTION

Figure 1:
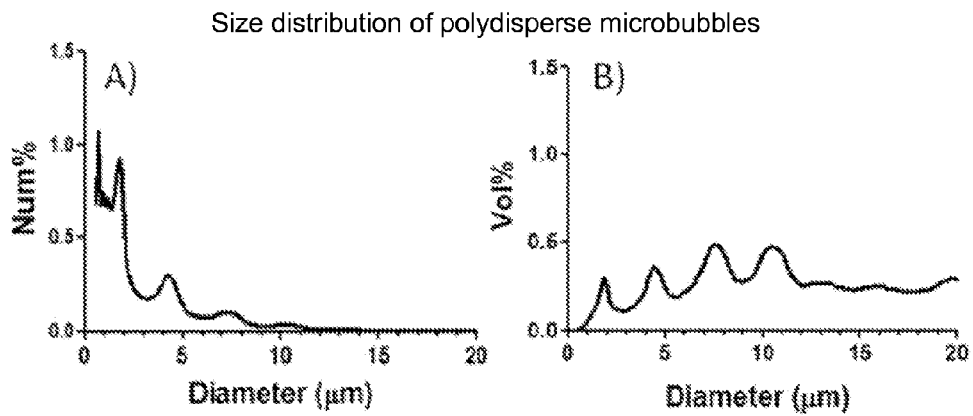
FIG. 1 is a graphical representation of number and volume size distribution of polydisperse microbubbles according to an embodiment of the disclosed subject matter.

Magnetic resonance imaging (MRI) and ultrasound imaging using microbubbles can be used as imaging modalities in diagnostic and drug therapy applications. Both imaging modalities may utilize contrast agents to enhance the signal to contrast ratio. MRI relies on the examination of different distribution and properties of water in observed tissues as well as the spatial variation of longitudinal (T1) and transversal (T2) relaxation times after excitation with a radio frequency pulse to produce images. MRI signal increases with 1/T1 and decreases with 1/T2. T1-weighted MRI has been more commonly used in the clinical setting.

The MRI contrast agents can be classified according to the relaxation processes they enhance. In particular, R1 (1/T1) contrast agents include paramagnetic materials, such as gadolinium ions ($Gd^{3+}$) or other lanthanide ions. The R1 contrast agents act to reduce the T1 time thereby producing positive contrast (i.e., brighter image). The R2 (1/T2) contrast agents reduce the T2 times and thus produce a negative contrast (i.e., darker image). Contrast agents that increase the ratio of R2/R1 are called susceptibility weighted agents, due to the greater loss of phase coherence caused by inhomogeneities in the magnetic field that produce longer T2 decay times above a normal baseline.

The relaxivity of T1-weighted contrast agents can be increased by binding to macromolecular substrates, such as, but not limited to, liposomes, dendrimers, and nanoparticles. Such complexes act as vesicles to increase loading of the MRI contrast agent and to reduce the tumbling rate of the contrast media so as to allow for a substantial increase in the relaxivity R1.

Gas-filled microbubbles can be used as contrast agents for ultrasound imaging and targeted drug delivery due to their compressible gas cores. As used herein, microbubbles refer to micron-sized spherical gas-filled particles, which can be stabilized by an organic coating, such as a lipid shell, at the gas-liquid interface. Microbubbles having a diameter of 10 μm or less can be generated and used as contrast agents. The gas cores of the microbubbles provide strong backscatter echo that can be detected using the ultrasound transducer. Depending on controlled ultrasound parameters, the microbubbles may cavitate stably or inertially, thereby allowing for imaging, targeting, controlled release, and vascular permeability enhancement. Microbubbles can also be destroyed by externally applied ultrasound of sufficient intensity so as to release shell material as well as any gas contained by the microbubble shell.

Microbubbles can also be used as magnetic resonance susceptibility contrast agents (i.e., reducing R1) in vivo due to the induction of large local magnetic susceptibility differences by the gas-liquid interface, thereby creating a negative contrast in the MRI image. This feature of the microbubbles described herein allows them to be utilized as ultrasound-triggered MRI contrast agents. The MRI signal can be spatially and temporally controlled via microbubble destruction by external acoustic forces, since the susceptibility-weighted (i.e., negative contrast) should disappear, or at least be reduced, with the destruction of the gas-liquid interface of the microbubble. Moreover, lanthanide ions that coated the microbubble remain with the now-destroyed lipid shell. Thus, the positive contrast can increase due to the presence of the paramagnetic contrast agent on the remnants of the microbubble shell. The resulting MRI image can evolve from a normal tissue contrast before microbubble destruction to a positive contrast after microbubble destruction.

Microbubble populations having different diameters or sizes can be isolated by centrifugation. These size-selected microbubbles can provide superior performance over polydisperse microbubble populations in imaging and biomedical applications, such as MRI-guided focused ultrasound (MRIg-FUS) therapy. For example, microbubbles can be sorted into size ranges of 1-2 µm, 4-5 µm, and 6-8 µm in diameter from an initially polydisperse suspension. The sorting of the microbubbles into separate size-based populations can be achieved by, for example, centrifugation. For a given centrifugal speed, a two-phase separation can occur, with the upper phase containing primarily larger microbubbles and the lower phase containing the less buoyant, smaller microbubbles. The larger microbubbles can have a faster rise velocity at a given centrifugal force than the smaller ones. The separation process can be adjusted for different microbubble populations by varying parameters, such as centrifugation speed, centrifugation time, column height, and initial suspension fraction.

Lipid-coated microbubbles can be prepared in high concentrations by acoustic emulsification of a suspension containing a mixture of a phospholipid and a lipo-polymer in the presence of an insoluble gas. For example, the phospholipid may be 1,2-distearoyl-sn-glycero-3-phosphoethanolamine (DSPE), the lipo-polymer may be 1,2-distearoyl-sn-glycero-3-phosphoethanolamine-N-[methoxy(polyethylene glycol)-2000] (DSPE-PEG2000), and the insoluble gas may be perfluorobutane.

Microbubbles can be coated with DSPE and DSPE-PEG2000 at a molar ratio of 9:1. The indicated amount of DSPE can be dissolved in a chloroform/methanol/water mixture and transferred to a container, such as a glass vial. The organic solvent mixture can then be evaporated with a steady stream of, for example, nitrogen while vortexing for 10 minutes followed by several hours under vacuum. 0.01 M NaCl phosphate-buffered saline (PBS) solution can be filtered using a 0.2-µm pore size polycarbonate filter. The dried lipid film can then be hydrated with the filtered PBS and mixed with DSPE-PEG2000 (e.g., 25 mg/mL in filtered PBS) to a final lipid concentration of 2.0 mg/m L.

The lipid mixture can be first sonicated with, for example, a 20-kHz probe at low power (e.g., approximately 3 W) in order to heat the pre-microbubble suspension above the main phase transition temperature of the phospholipid (e.g., for DSPE about 74° C.) and further disperse the lipid aggregates into small unilamellar liposomes. PFB gas can then be introduced by flowing it over the surface of the lipid suspension. Subsequently, high power sonication (e.g., approximately 33 W) can be applied to the suspension for about 10 seconds at the gas-liquid interface to generate microbubbles therein. Of course, other microbubble fabrication techniques may also be used to form the microbubbles described herein.

The initial microbubble population can be determined by light extinction. FIG. 1 shows number % and volume % of an exemplary polydisperse population of microbubbles after acoustic emulsification as a function of diameter. As is evident from the number-weighted distribution of FIG. 1 the larger diameter size microbubbles are present in the polydisperse population to a lesser degree than the smaller sizes after emulsification.

Figure 2:
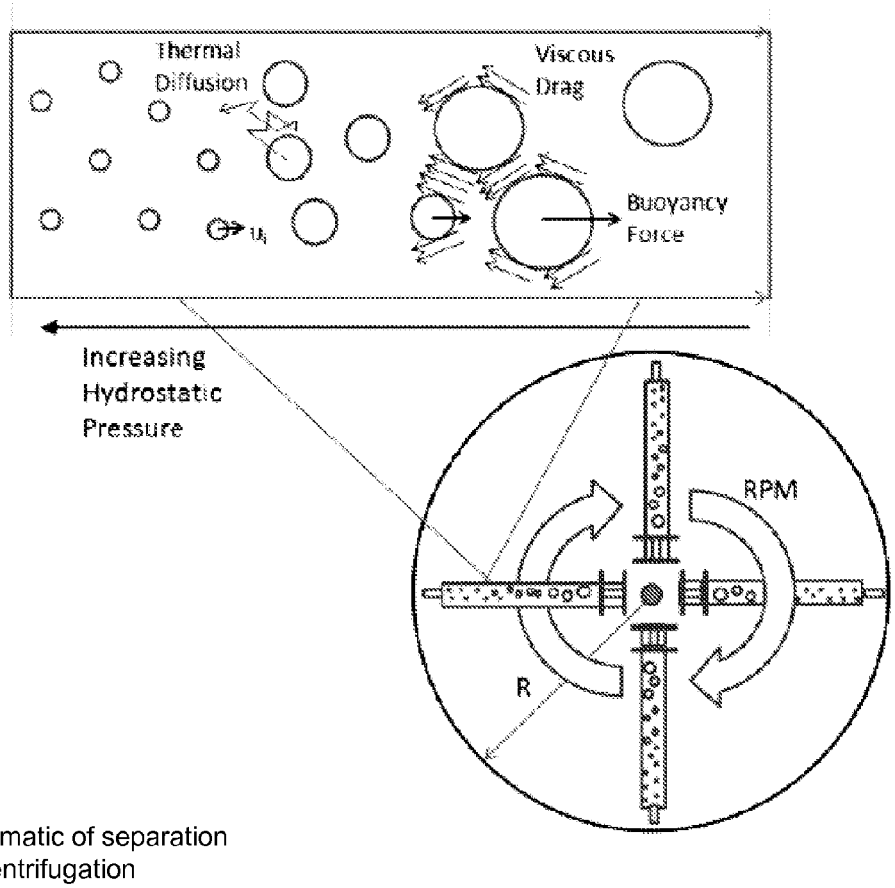
FIG. 2 is a schematic representation of separation by centrifugation according to an embodiment of the disclosed subject matter.

Centrifugation can be used to select microbubbles having a certain diameter from other microbubbles based on their migration in a centrifugal field, as illustrated schematically in FIG. 2. Centrifugation conditions can be determined based on initial microbubble size distribution and concentration. For a given initial size distribution, time period, and syringe column length, the strength of the centrifugal field (in RCF) can be calculated using the following equations:

$$u_i = \frac{2(\rho_2 - \rho_{1i})}{9\mu} R_i^2 g, \qquad (1)$$

$$\frac{\mu_2^*}{\mu_2} = 1 + 2.5\Phi + 7.6\Phi^2, \qquad (2)$$

$$\Phi = \sum_{i=1}^{N_d} \Phi_i, \qquad (3)$$

where $\Phi$ is the total microbubble volume fraction for N size classes, $R_i$ is the particle radius, g is gravity, $\mu$ is viscosity, $\rho_2$ is the density of the fluid, $\rho_{1i}$ is the density of the particulate, and i refers to the particle size class. Volume fraction can be assumed constant over the entire column and acceleration/deceleration effects can be neglected.

Figure 3:
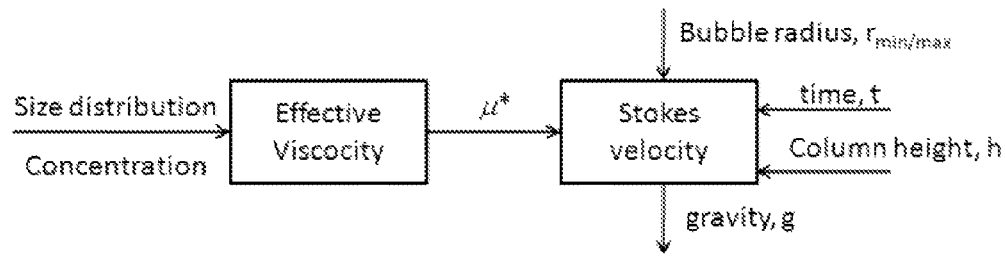
FIG. 3 is a schematic representation of microbubble size isolation according to an embodiment of the disclosed subject matter.

Following production, microbubbles can be collected into syringes, for example 30 mL syringes having a length of approximately 8.2 cm. Larger size class microbubbles (e.g., diameters greater than 1 µm) can be separated from submicron particles and vesicles by applying centrifugal force using a bucket-rotor centrifuge, for example, such that 1 µm bubbles rise from the bottom to the top of the column. Centrifugation at 300 RCF (relative centrifugal force) for 5 minutes was performed to collect all microbubbles from the suspension into a cake resting against the syringe plunger. The resulting concentrated microbubble cake can then be re-dispersed into 30 mL of filtered phosphate buffered saline (PBS) solution and the infranatant discarded. The initial suspension volume fraction can be adjusted to 5-10%. A schematic of a protocol that can be used for determining the RCF for size selection is illustrated in FIG. 3.

Figure 4:
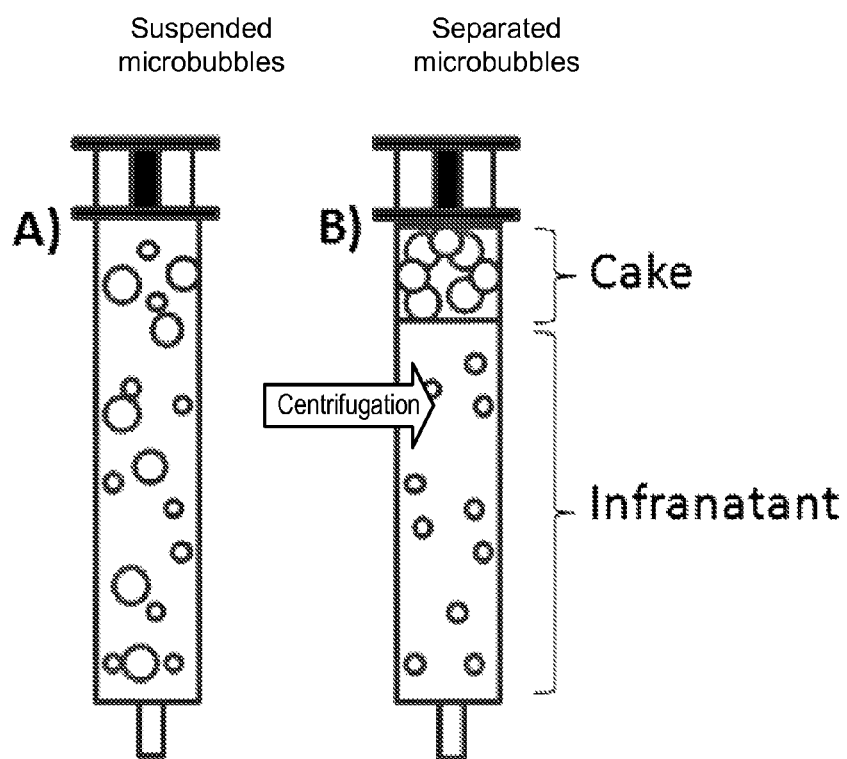
FIG. 4 is a schematic representation of microbubble size separation according to an embodiment of the disclosed subject matter.

For a specific microbubble size, the calculated RCF needed for the microbubbles to rise from the bottom to the top of the syringe column is applied to the polydisperse solution for a predetermined period of time, e.g., one minute. After centrifugation, microbubbles above the specified size will be incorporated into the cake, while a fraction of the total microbubbles less than the desired cutoff will remain in the infranatant, as schematically illustrated in FIG. 4.

Figure 5:
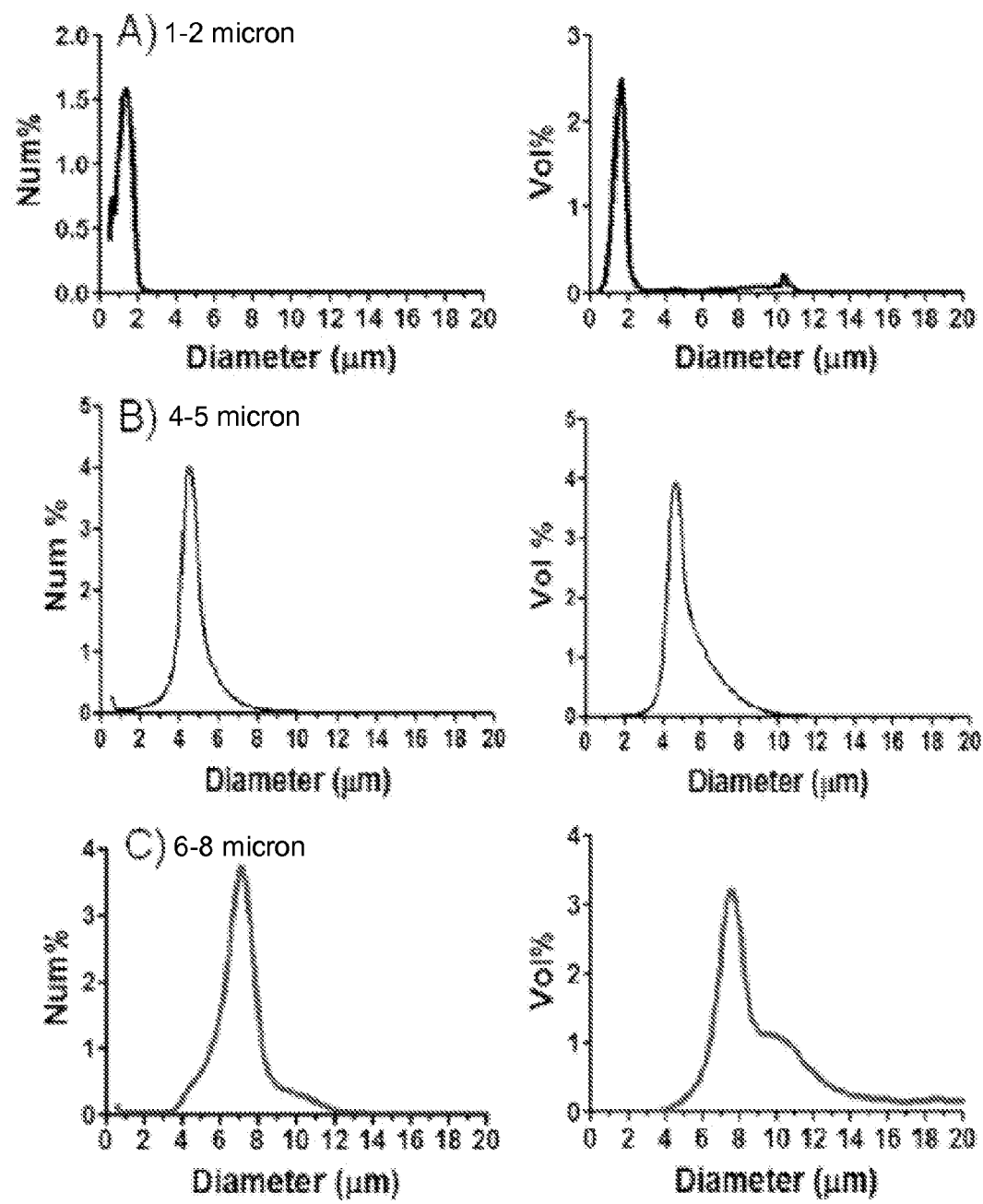
FIG. 5 is a graphical representation of size distribution of three exemplary size-sorted microbubble populations.

For the selection of smaller microbubble populations (e.g., 1-2 µm in diameter), the infranatant can be kept and concentrated. For the selection of microbubbles of larger size (e.g., greater than 2 µm in diameter), the process can employ multiple steps. For example, in selecting the 4-5 µm diameter microbubble population, the population of microbubbles having diameters less than 4 µm can be removed from the polydisperse solution by repeated centrifugation cycles at calculated RCF and discarding the infranatant after each cycle. Multiple cycles of centrifugation, e.g., 5-8 cycles, may be necessary in order to remove substantially all of the smaller microbubbles from the desired larger size microbubble population. After isolating the microbubbles having diameters greater than 4 µm, the population of microbubbles having diameters greater than 5 µm can be removed from the solution. The cake from the first step, which includes microbubbles having diameters greater than 4 µm, can be re-suspended. The RCF calculated for 5 µm diameter microbubbles to rise to the top of the column can then be applied to the suspension. The infranatant, which includes microbubbles having a diameter in the 4-5 µm range, can be kept and concentrated. A similar protocol can be applied to microbubbles of any desired size range, such as 6-8 µm diameter microbubbles. FIG. 5 shows the size distribution (in number percentage and volume percentage) of three exemplary size-sorted microbubbles populations separated using the above process. Microbubble size distribution can be determined by laser light obscuration and scattering.

For microbubbles to be useful for MRIg-FUS as well as other applications, it would be helpful to their performance if the microbubble populations maintained their size distribution and are otherwise stable. Stability affects shelf life and biodistribution. The degradation of microbubble suspensions can be attributed to Ostwald's ripening, which is the process by which large particles can grow at the expense of smaller ones. Ostwald's ripening is driven by the differences in solubility due to differences in curvature of particles. Small particles shrink due to enhanced solubility arising from their high curvature while larger particles grow. The ripening process can reach a stationary regime, where the form of the particle size distribution is achieved. In this regime, particle growth may be linear with respect to time, and the number average radius can be equivalent to the critical radius of particle growth. A microbubble particle may grow if it is above the critical radius, whereas microbubbles below the critical radius may shrink. The growth (or shrinkage) rate of microbubbles may be affected by surfactant type, the presence of vesicles, as the polydispersity of the microbubbles.

Ostwald's ripening is driven by differences in solubility of different emulsion radii. Thus, a polydisperse microbubble population may ripen at a more appreciable rate than a substantially monodisperse microbubble population. Size-selected microbubble populations may maintain their size distribution better than polydisperse suspensions. Moreover, as the microbubble radii more closely approach the critical radii, the growth rate of the microbubbles may get closer to zero.

The rate of ripening may also depend on surfactant concentration. For example, sodium dodecyl sulphate (SDS) and a phospholipid surfactant may be used to alter the rate of ripening. SDS is a soluble surfactant whose surface tension (e.g., 30 mM/m) can be assumed constant above its critical micelle concentration (CMC). In contrast, the surface tension of the phospholipid surfactant on a microbubble is not constant such that the surface tension changes as the microbubble shrinks or expands. Above their CMC, the surfactants may form vesicles. Due to different shape factors, SDS tends to form micelles while phospholipids tend to form bilayers. These vesicles and micelles may also influence the growth rate of the microbubble populations.

MRI-detectable microbubbles can be designed for MRIg-FUS therapy. MRIg-FUS therapy utilizes high intensity focused ultrasound (HIFU) to ablate tissue and MRI to monitor the thermal dosage applied. Applications for MRIg-FUS include, but are not limited to, monitoring the heating of muscle tissue during (HIFU) and treatment of uterine fibroids, as well as treatment of liver-, bone-, prostate-, and brain-related diseases. In addition to heating, ultrasound can produce other therapeutic bioeffects. At high acoustic intensities, microbubbles may be formed in the focal area during the rarefaction phase of the ultrasound wave by inception cavitation. These bubbles may grow unstably and undergo transient collapse, or inertial cavitation, producing jets and shockwaves that enhance heating at the focus. However, the formation of these inception microbubbles can be unpredictable, and inertial cavitation may lead to damage of tissue outside the desired region.

In MRIg-FUS, the potential for damage can be reduced by using preformed lipid-coated microbubbles, such as the microbubbles described herein. These microbubbles can have a lower acoustic intensity threshold for ablation, thereby minimizing the thermal buildup of heat in surrounding tissue that can be associated with high intensity focused ultrasound (HIFU). Moreover, the lipid-coated microbubbles can be used as a contrast agent for ultrasound imaging due to their compressible gas cores, which render the microbubbles echogenic. Depending on ultrasound parameters, the lipid-coated microbubbles may cavitate stably or inertially thereby allowing for imaging, targeting, controlled release of microbubble payloads (e.g., the gas core of the microbubble), and vascular permeability enhancement. The microbubbles may also enhance drug delivery via contract stress due to gas expansion or shear stress due to liquid flow around the microbubble.

One application for MRIg-FUS with microbubbles is in the opening of the Blood-Brain-Barrier (BBB). The BBB acts a permeability barrier in the blood capillary endothelium that prevents most molecules in the blood greater than 400 Da from penetrating into the brain. Since many drugs are greater than 400 Da, the BBB effectively prevents the treatment of neurodegenerative diseases, such as Parkinson's, Huntington's, and Alzheimer's. However, microbubbles when used with FUS can lead to a localized, noninvasive, and transient opening of the BBB. The opening of the BBB can then be detected by MRI while using an appropriate contrast agent, such as a T1-weighted MRI contrast agent.

For MRIg-FUS therapy applications, a paramagnetic lanthanide, such as gadolinium ($Gd^{3+}$), can be loaded through chelation to a macrocyclic ligand molecule that is conjugated to the lipid shell of the microbubble. The lanthanide is a contrast agent for T1-weighted MRI whose in vivo toxicity can be reduced via the chelation to the macrocyclic ligand. The amount of lanthanide in the microbubble shell can be measured, for example, using optical emission spectroscopy. The relaxivity of the lanthanide can be increased by binding the lanthanide to macromolecular or colloidal substrates, such as, but not limited to, liposomes, dendrimers, and nanoparticles. These complexes increase the relaxivity by slowing down the molecular tumbling rate of the lanthanide. The attachment of the lanthanide to the lipid shell of the microbubble may also slow down the tumbling rate and/or increase $\tau_R$ by increasing the rigidity and size of the complex. The centrifugal separation technique described above allows selection of microbubbles having a larger surface area for the attachment of the lanthanide.

The intrinsic gas/liquid interface of the microbubble can also cause a local inhomogeneity in the magnetic field under MRI, which reduces T1 signal and produces a negative contrast (i.e., darker image). The microbubbles can thus act as magnetic resonance susceptibility contrast agents in vivo due to the magnetic susceptibility differences at the gas-liquid interface, thereby causing a positive contrast in T2- and a negative contrast in T1-weighted MRI. The negative T1-contrast nature of the microbubbles allows them to be utilized as ultrasound triggered MRI contrast agents. When the microbubble is intact with a gas core, the contrast enhancement of the lanthanide-bound shell is minimal. However, when the microbubble is fragmented and the gas core is dissolved, the fragmented shell that is left behind can increase the T1 signal, thereby resulting in a positive contrast (i.e., brighter image). The T1-weighted MRI signal can be spatially and temporally controlled via the destruction of the microbubbles by external acoustic forces, since the negative contrast should dissipate with the absence of the gas-liquid interface after microbubble destruction. Moreover, the positive contrast should increase due to the presence of the paramagnetic lanthanide on the remnant shell material. In other words, the image should change from a normal tissue contrast to a positive contrast as the microbubbles are destroyed by externally applied acoustic signals. As a result, lanthanide-bound microbubbles can provide MRI-based detection of the location and dose of focused ultrasound during MRIg-FUS by providing MRI visualization of ultrasound-induced microbubble destruction.

Figure 9:
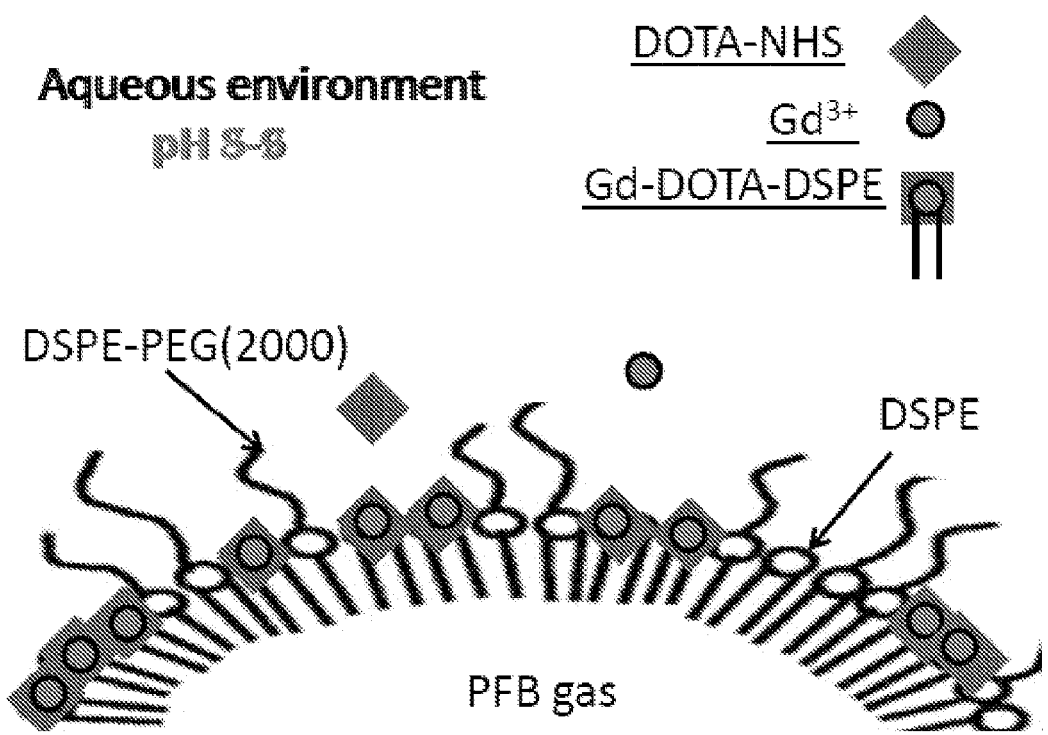
FIG. 9 is a schematic representation of a post-labeled microbubble.

Microbubbles with paramagnetic lanthanide-bound shells can be fabricated using a post-labeling technique, as shown in FIG. 9. The macrocyclic ligand DOTA_NHS can be conjugated to the amine group of the DSPE in the shell of size-selected microbubbles, followed by chelation of lanthanide.

The lanthanide can be bound to the lipid shell of the microbubbles by functionalizing the microbubble shell with a macrocyclic ligand. The ligand can react with the primary amino group on the DSPE lipid shell and serves to reduce the in vivo toxicity of the lanthanide, which could otherwise block calcium channels in vivo. For example, the ligand may be 1,4,7,10-Tetraazacyclododecane-1,4,7,10-tetraacetic acid (DOTA) or 1,4,7,10-Tetraazacylcododecane-1,4,7,10-tetraacetic acid mono(N-hydroxysuccinimide ester) (DOTA-NHS).

The ligand DOTA-NHS contains an NHS ester active group, which is a hydrophilic active group that couples rapidly with primary amines on target molecules. The NHS-ester can react with the nucleophilic amine residue to create a stable amide linkage. The microbubble suspension can be buffered to slightly basic conditions to make the primary amine more nucleophilic, thereby increasing its reactivity with the electrophile on DOTA-NHS. NHS esters can have a half-life on the order of hours a physiological pH. However, the amine reactivity and rate of hydrolysis can increase with pH. To minimize the hydrolysis rate, a high concentration of active group amine can be provided by concentrating the microbubble suspension.

The degree of modification to produce optimal product can also be controlled by adjusting the ratio of NHS-esters to target amine molecules. Using microbubble size information, such as obtained via light extinction, the total microbubble surface area in the microbubble population can be calculated. The average projected area per lipid molecule for the lipid DSPE can be approximated as 0.44 nm$^2$. The total number of lipid molecules on the microbubble shell surface can then be calculated. The relative lipid molar ratio in bulk solution can be approximately the same as for the microbubble shell. Based on the molar percentage of amine residue, a 50 molar excess amount of NHS-esters can be provided for conjugation.

After conjugation of the metal chelating ligand (e.g., DOTA) to the microbubble shell, the paragmagnetic lanthanide ion (e.g., Gd$^{3+}$Z) can be bound to the microbubble shell via a chelation reaction to form, for example, DSPE-DOTA-Gd. DOTA and a lanthanide such as Gd$^{3+}$ can form a complex with a high thermodynamic stability and low dissociation rate. The rate at which DOTA forms a complex with a lanthanide can depend on many factors including pH, temperature, and concentration of the reactants. An optimal buffer range for this reaction can be within a pH of 5-6, since above pH 6 lanthanides may start to form insoluble hydroxylated species.

Gadolinium forms $Gd(H_2O)_8^{3+}$ in aqueous solution at pH 5-6. During chelation, most of the water molecules are displaced form the inner-sphere of the Gd$^{3+}$ ion by more basic donor atoms of DOTA, including amines (e.g., NH$_3$) or carboxylates (e.g., COOH) except for one which remains bound to Gd$^{3+}$. The lone water binding site can be important for MRI contrast since it allows a large number of water molecules to experience the magnetization from Gd$^{3+}$ each second via chemical exchange thereby increasing relaxivity.

The formation of the complex can be a relatively slow process at room temperature, and the rate determining step can involve the base assisted rearrangement of the intermediate complex into the final complex. To increase the rate of complexation, the reaction contents can be heated to a temperature about 5-10° below the main phase transition temperature ($T_m$) of the lipid component (e.g., for DSPE, $T_m$=74° C.) for 1-2 hours. Microbubbles coated with DSPE can be stable at such conditions without substantial change in size distribution and concentration. After the chelation reaction, excess lanthanides can be removed by washing the microbubbles one or more times via centrifugation.

The amount of lanthanide chelated can be determined by, for example, inductively-coupled plasma optical emission spectrometry (ICP-OES). ICP-OES is an analytical technique used for the detection of trace metals. It is a type of emission spectroscopy that uses the inductively coupled plasma to produce excited atoms and ions that emit electromagnetic radiation at wavelengths characteristic of a particular element. The intensity of this emission is indicative of the concentration of the element within the sample. The ICP-OES allows for the determination of the lanthanide concentration within the sample.

Figure 6:
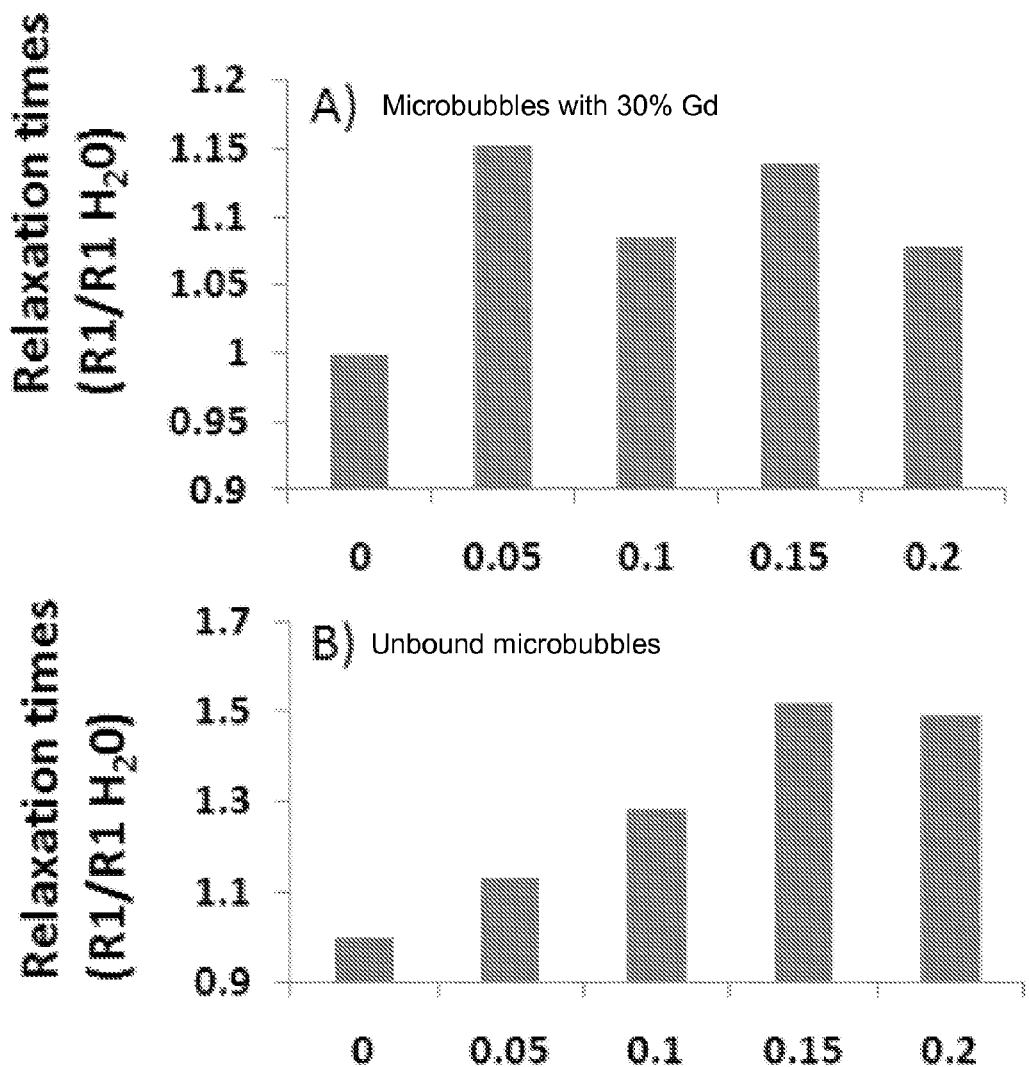
FIG. 6 is an exemplary comparison of T1 times of gadolinium bound and unbound microbubbles.
Figure 7A:
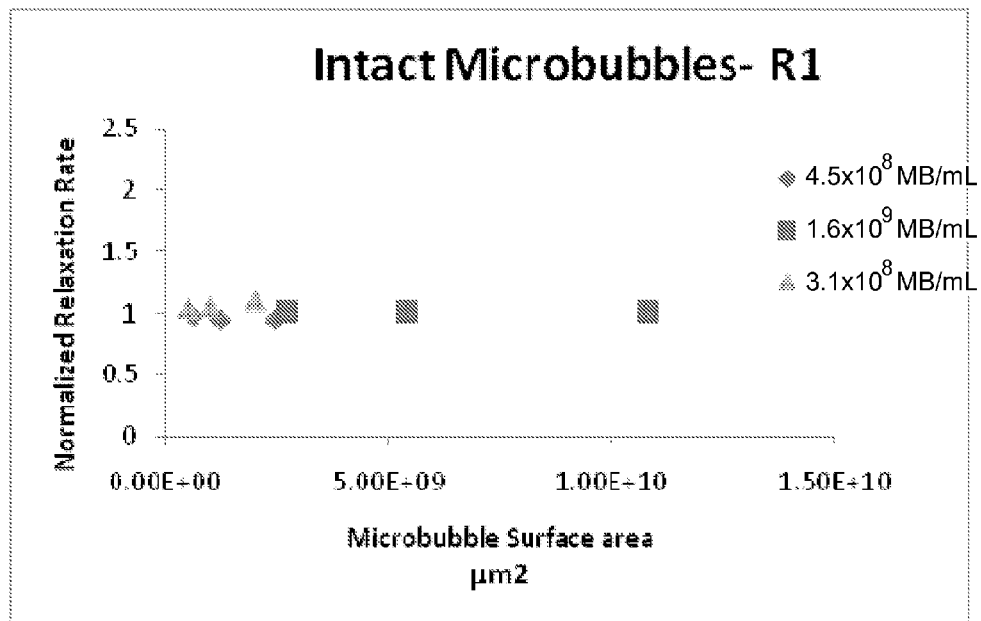
FIGS. 7A and 7B are exemplary relaxation rates for intact and destroyed microbubbles.
Figure 7B:
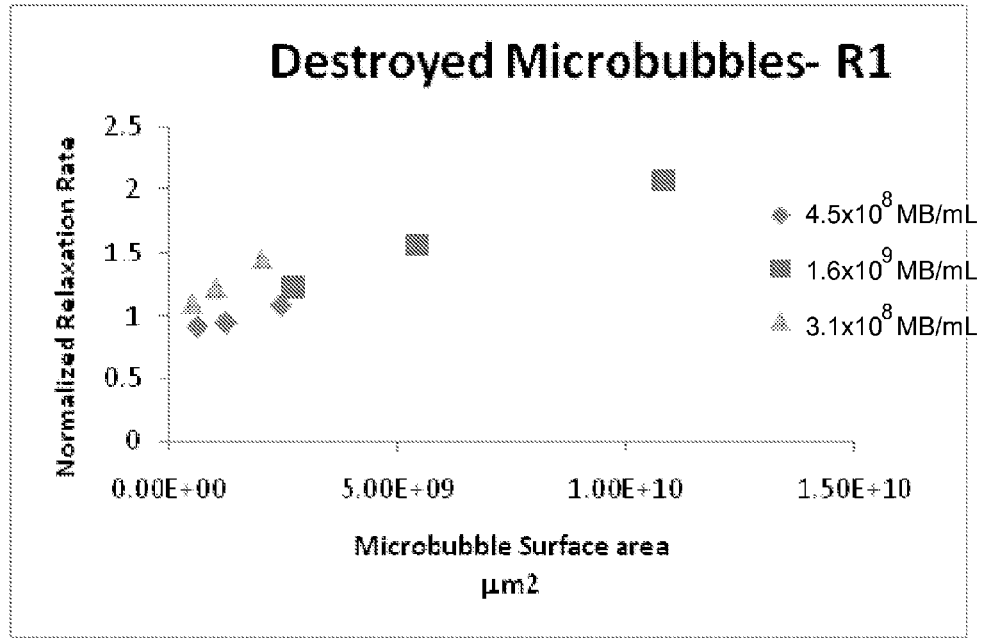
Figure 8A:
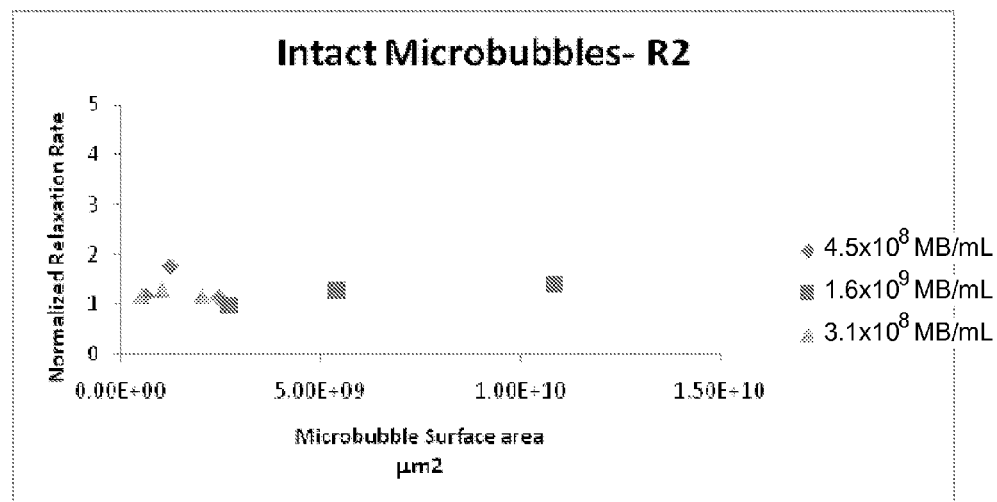
FIGS. 8A and 8B are exemplary relaxation rates for intact and destroyed microbubbles.
Figure 8B:
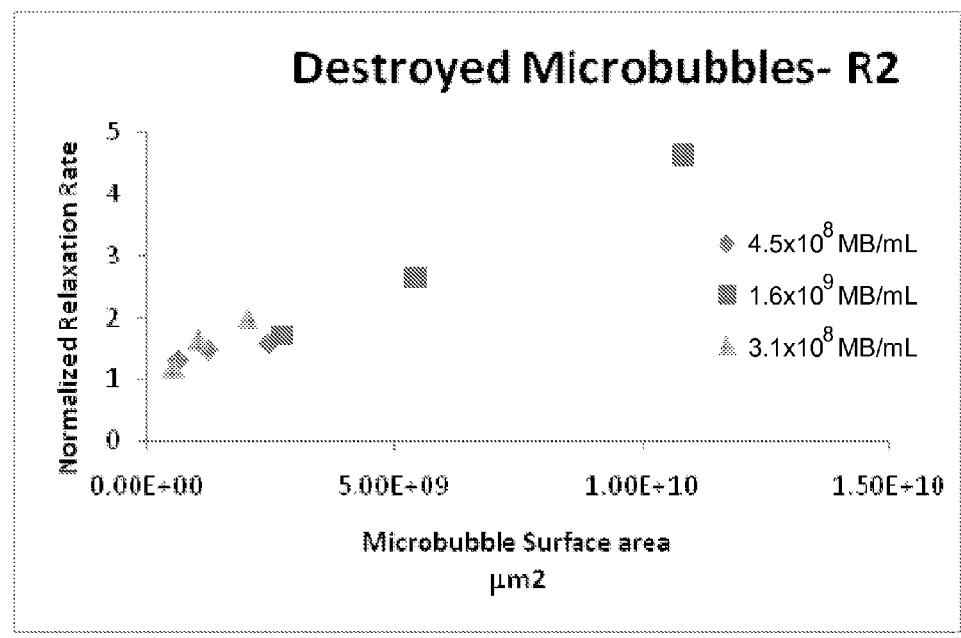

As discussed above, the presence of paramagnetic lanthanide, such as Gd$^{3+}$, on the microbubble shell can reduce the longitudinal relaxation times and produce greater signal strength after microbubble dissolution. Relaxivity of the lanthanide-bound lipid shell can be determined by varying the concentration of the samples and by measuring the T1 relaxation times with de-ionized water as a reference. The T1-weighted relaxivity, $r_1$, is determined from the slope of the plot of $(1/T1)_{obs}$ versus concentration of the lanthanide on the microbubble shell and is expressed in units of m/(Ms). The T1-weighted relaxivity, $r_1$, can be calculated from:

$$\left(\frac{1}{T_1}\right)_{obs} = \left(\frac{1}{T_1}\right)_d + r_1 [Gd], \quad (4)$$

where $(1/T1)_{obs}$ is the observed T1-weighted relaxivity, $(1/T1)_d$ is the diamagnetic contribution or relaxation rate of tissue, $(1/T1)_p$ is the paramagnetic (e.g., Gadolinium) contribution to relaxivity and [Gd] is the concentration of the Gd$^{3+}$. FIG. 6 shows the T1 times of both 4-5 μm diameter microbubbles containing 30% Gd$^{3+}$ and unbound microbubbles for comparison. As is apparent from the figure, unbound microbubbles reduce the T1 signal whereas Gd-bound microbubbles have minimal effect on contrast enhancement. The application of an ultrasonic destruction pulse to the microbubbles removes the gas-liquid interface, thereby resulting in an increase in the T1 signal due to the remnant shell containing only the paramagnetic Gd-DOTA complex. This is illustrated in the results of FIGS. 7A-7B and 8A-8B, where destroyed microbubbles show a greater normalized relaxation rate than corresponding intact microbubbles. Of course, other imaging or contrast applications for the gas-filled microbubbles beyond the MRIg-FUS application described herein are also possible according to one or more contemplated embodiments.

In an exemplary embodiment, the effect of $Gd^{3+}$-bound microbubbles on the $T_1$ and $T_2$ relaxation times was determined using MR relaxometry. Intact and fragmented $Gd^{3+}$-bound microbubbles were mixed with saline in four different volume ratios (0, 25, 50 and 100%) creating 200 µL solutions, which were placed in MR-compatible tubes with an inner diameter of 0.5 cm. Intact and fragmented 4-5 µm DOTA-bound microbubbles without $Gd^{3+}$ binding were used as controls. A 9.4 T vertical MRI system (Bruker Biospin, Billerica, Mass.) was used to acquire turbo spin echo (RARE-VTR) images with variable repetition times (from 300 to 12,500 ms) and multi-slice multi-echo (MSME) images with variable echo times (from 20 to 320 ms) for $T_1$ and $T_2$ mapping, respectively. Eight 1.5 mm-thick, axial slices with a field of view (FOV) of 15×15 mm$^2$ (matrix size: 96×96) covered the entire solution in each tube. Each slice depicted a slab of all four solutions at a specific height. $T_1$ and $T_2$ relaxation maps of each slice were derived using the Image Processing Toolbox of MATLAB R2008b (MathWorks Inc., Natick, Mass.). The first and last slice were not taken into account in the relaxation measurements, since the MR signal coming from these slices was contaminated by the void below and over the solution. The pixel-by-pixel estimations yielded the $T_1$ and $T_2$ maps, respectively. Four pre-defined, identical, circular regions of interest (ROI) of 2.35 mm in diameter were selected on each slice, in order to measure the relaxation rate of each solution throughout the tube. Each ROI covered a large surface area within the limits of the tube. Six measurements were made for each tube (from slice 1 to 6) and the mean value yielded the $T_1$ or $T_2$ relaxation times for each solution.

The size isolation protocol yielded 4-5 µm diameter microbubbles at a concentration a least $2 \times 10^9$ MB/mL. After DOTA conjugation, microbubble concentration and number-weighted median diameter deviated by less than 1%. In this study, chelation reactions were not carried out at room temperature due to the observed lack of adequate $Gd^{3+}$ binding to DOTA at this condition and because the rate of chelation of $Gd^{3+}$ to DOTA was found to increase at elevated temperatures and proton concentrations. After chelation at 50° C. and pH 5.6, microbubble concentration decreased by ~50% while the number-weighted median diameter deviated by less than 1%. After chelation at 70° C., however, microbubble concentration decreased by ~65% while the number-weighted median diameter also decreased by ~30%. From ICP-OES analysis, the $Gd^{3+}$ chelation on the microbubble shell occurring at 50° C. and 70° C. was $7.0 \times 10^5 \pm 1.6 \times 10^5$ (mean±standard deviation) and $7.5 \times 10^5 \pm 3.0 \times 10^5$ ions/µm$^2$, respectively. Therefore, all subsequent chelation reactions were carried out at 50° C. since the size distribution of microbubbles was maintained at this temperature without affecting the degree of $Gd^{3+}$ binding. Under these conditions, the average $Gd^{3+}$ loading was $3.6 \times 10^7 \pm 1.0 \times 10^7$ ions/microbubble or approximately 40% of the DSPE lipid molecules in the monolayer shell. ICP-OES analysis also determined that negligible amounts of $Gd^{3+}$ bound to lipid-coated microbubbles without DOTA.

Fragmented microbubbles were produced by the removal of the gas core of intact microbubbles through bath sonication and heating. As observed from both the $T_1$- and $T_2$-weighted MRI maps, the control DOTA-without $Gd^{3+}$ microbubbles (intact and destroyed) produced an MRI signal response similar to baseline (saline), which did not deviate significantly with an increase in microbubble concentration. The intact $Gd^{3+}$-bound samples produced similar MR signal intensities as saline and control microbubbles, and the signal intensity was not dependent on an increase in sample concentration. Similarly, it was observed that the relaxation rate did not increase versus increasing intact $Gd^{3+}$-bound microbubble concentration, and the signal response produced was similar to that of control samples.

The fragmented $Gd^{3+}$-bound microbubbles, however, resulted in a noticeable increase in MRI signal intensities compared to saline, control and intact $Gd^{3+}$-bound microbubbles. Additionally, the effect was concentration-dependent, with an increase in fragmented $Gd^{3+}$-bound sample concentration leading to an increase in MRI signal intensity. These results suggest that the MR signal came primarily from the $Gd^{3+}$ groups and not the other components of the lipid microbubble shell, and the relaxation rate appeared to be most strongly related to the state of the microbubble (i.e., intact vs. fragmented).

Molar relaxivities (mM$^{-1}$ s$^{-1}$) were also calculated. The longitudinal molar relaxivity ($r_1$) increased by ~200% going from fragmented control DOTA-bound microbubbles to fragmented $Gd^{3+}$-bound microbubbles. The transversal molar relaxivity ($r_2$) increased by ~300% going from fragmented control DOTA-bound without $Gd^{3+}$ microbubbles to fragmented $Gd^{3+}$-bound microbubbles. Both $r_1$ and $r_2$ for the fragmented $Gd^{3+}$-bound microbubbles were similarly greater than the corresponding values for the intact $Gd^{3+}$-bound microbubbles. The average $r_1$ and $r_2$ values for the fragmented microbubbles were $4.2 \times 10^8$ and $1.3 \times 10^{10}$ mM$^{-1}$ s$^{-1}$ per microbubble, respectively.

Thus, chelation of the paramagnetic lanthanide $Gd^{3+}$ to the ligand, DOTA, bound on the surface of lipid-shelled microbubbles was achieved at a reaction temperature of 50° C. without degrading 4-5-µm microbubble size distribution. Under both $T_1$ and $T_2$-weighted MRI characterization in vitro, the intact microbubble monolayer configuration of the $Gd^{3+}$-DOTA microbubbles provided MRI signal enhancement similar to baseline saline. However, the liposomes produced from fragmentation of the $Gd^{3+}$-bound microbubbles resulted in significant increase in the MRI signal. Furthermore, the relaxivity of the resulting $Gd^{3+}$-bound liposomes were slightly higher than those of commercially available MRI contrast. The inherent differences in MRI signal intensities between intact and fragmented $Gd^{3+}$-DOTA bound microbubbles can be beneficial for MRIg-FUS therapy applications.

Although particular configurations have been discussed herein, other configurations can also be employed. Furthermore, the foregoing descriptions apply, in some cases, to examples generated in a laboratory, but these examples can be extended to production techniques. For example, where quantities and techniques apply to the laboratory examples, they should not be understood as limiting. In addition, although the production of oxygen microbubbles has been specifically described herein, other gases (elemental or compositions) are also possible according to one or more contemplated embodiments.

In various embodiments, pre-formed microbubbles can be used as cavitation nuclei to lower the acoustic intensity threshold required for tissue ablation with focused ultrasound therapy (FUS), thereby lowering the thermal buildup in surrounding tissue.

Intravenously administered microbubbles may also be used to enhance vascular permeability for targeted drug and gene delivery. For blood-brain barrier (BBB) opening applications, an MRI-detectable microbubble formulation can be used to measure microbubble concentration, image cavitation events, and to determine the biodistribution of microbubble shell debris following FUS.

In various embodiments, it is disclosed a method and system for using paramagnetic lanthanide-bound microbubbles to spatially and temporally control a magnetic resonance imaging (MRI) signal via microbubble fragmentation. In other embodiments, using microbubble cavitation as a MRI biosensor is disclosed to monitor and minimize the side effects associated with high intensity focused ultrasound (HIFU).

Various embodiments include a method of controlling an imaging signal through microbubble fragmentation, comprising (including): introducing pre-fabricated microbubbles into a portion of a host; bursting the microbubbles using an external acoustic force; and imaging the portion of the host using an imaging device. The microbubbles can include a paramagnetic inhomogeneity at the gas-liquid interface when intact, and the paramagnetic inhomogeneity can be eliminated by the bursting of the microbubbles. During fragmentation of the microbubbles, the imaging signal changes from a negative contrast to a positive contrast. Therefore, the imaging signal can be controlled based on a state (e.g., intact or fragmented) of the microbubbles.

The imaging signal intensity increases with an increase of the concentration of the fragmented microbubbles. Therefore, the imaging signal intensity can also be controlled by controlling the concentration of a paramagnetic lanthanide bound to the fragmented microbubble membrane.

In various embodiments, the microbubbles include a lipid coated membrane enveloping a fluid, the paramagnetic inhomogeneity being generated by a paramagnetic lanthanide bound to a surface of the lipid-coated membrane. The paramagnetic lanthanide is bound to the surface of the membrane by post-labeling. The post-labeling can include functionalizing the membrane with a macrocyclic ligand and loading the paramagnetic lanthanide through chelation to the macrocyclic ligand which is conjugated to the membrane. Post-labeling methods may include generating microbubbles with a ligand expressed on a surface for binding with the label and may further include storing the microbubbles for a time such as days or weeks and then reconstituting by diluting a stored cake for post-labeling thereafter.

According to embodiments, microbubbles are generated by flowing a precursor solution into a reaction volume of a continuous flow or batch sonicator and flowing a gas into the reaction volume at a same time. The precursor and gas are ultrasonically agitated to generate a flow of microbubbles with a wider size distribution than a target size distribution. This can be done in a continuous flow arrangement or a batch arrangement according to know engineering principles. The microbubble solution may then be size sorted, for example, using differential flotation column, a batch or continuous centrifuge, or other device. For example, a container may be filled with the generated microbubble solution after filling, isolating size compartments in the container, each compartment containing a different size population of the generated microbubbles. The container may be a rigid container or a flexible bag and compartments may be isolated using a clamp at different heights of the bag. The size-isolated microbubbles may next be concentrated to form a cake. The cake may be stored and the microbubbles may then be recovered by diluting in a solution and post-labeling. The microbubbles may be collapsed under external pressure to strengthen them.

Prior to introducing the microbubbles into the host, the microbubbles can be size-selected to create a batch having a predetermined size range. Note that, in addition to the column and container methods, the pre-selecting process can comprise collecting the microbubbles in a syringe and applying centrifuging the syringe to separate microbubbles having a predetermined size from other microbubbles.

In various embodiments, a system and method of real-time monitoring of location, intensity and dose of ultrasound energy deposition in a tissue is disclosed, the method comprising: introducing pre-fabricated microbubbles into a portion of a host; bursting the microbubbles using ultrasound; and imaging the portion of the host using an imaging device. The imaging can include visualizing the ultrasound-induced microbubble destruction using magnetic resonance imaging. The microbubbles can include a membrane enveloping a fluid and a material bound to the membrane which is capable of creating a magnetic inhomogeneity at the gas-liquid interfaces of the microbubbles. When the microbubbles are destroyed, the magnetic inhomogeneity disappears and the image changes from a negative to a positive image contrast based on a concentration of the material remaining on the fragmented microbubbles. The paramagnetic lanthanide can include gadolinium Gd3+.

The method can further include monitoring release of a substance included in the microbubbles. The substance can be a medical drug or a gene.

In various embodiments, a method of producing an image is disclosed, comprising: creating a magnetic inhomogeneity at gas-liquid interfaces of size-selected lipid-coated microbubbles by post-labeling; introducing the resulting microbubbles into a portion of a host; and imaging the portion of the host using an electromagnetic scanner.

In various embodiments, a system for producing an image is disclosed, comprising: a microbubble generator to generate lipid-coated microbubbles including a membrane enveloping a fluid and a material bound to the membrane, the material being capable of creating a magnetic inhomogeneity at the gas-liquid interfaces of the microbubbles; and an imaging device to image a portion of a host after insertion of the lipid-coated microbubbles into the host. The imaging device can include an electromagnetic imaging device, such as, but not limited to, a magnetic resonance imaging device. The microbubble generator can include a device that generates microbubbles that envelope a gas and have a membrane material which includes a paramagnetic material such as, but not limited to, gadolinium. The system can further comprise an ultrasound device configured to destroy microbubbles after insertion into the host.

A method of preparing a plurality of paramagnetic material-bound lipid microbubbles, each microbubble having a predetermined size range, is also disclosed. The method can comprise: preparing a plurality of microbubbles, each microbubble including a lipid coated membrane encapsulating a fluid; inserting the lipid-coated microbubbles into a holding device; separating the microbubbles having a size within the predetermined size range from the rest of the microbubbles by applying centrifugation on the holding device; removing the separated microbubbles having the predetermined size range from the holding device; and labeling the separated microbubbles with a paramagnetic material. The labeling can include: functionalizing the membranes of the separated microbubbles with a macrocyclic ligand; and loading the paramagnetic material through chelation to the macrocyclic ligand which is conjugated to the membranes.

The preparing can further include: acoustically emulsifying a suspension including a mixture of a phospholipid and a lipo-polymer in the presence of an insoluble gas. The emulsifying can include: dissolving the phospholipid in a chloroform/methanol/water mixture; evaporating the mixture to obtain a dried lipid film; hydrating the lipid film with a mixture including filtered phosphate-buffered saline solution (PBS) and the lipo-polymer to obtain a final lipid concentration; heating through sonication the lipid mixture to a temperature above a phase transition temperature of the phospholipid to disperse lipid aggregates into unilamellar liposomes; introducing the insoluble gas over the surface of the lipid mixture; and sonicating the lipid mixture at the gas-liquid interface to generate microbubbles therein.

In various embodiments, an imaging system is disclosed for performing an imaging method as described in any of the methods above. The imaging system can be used for monitoring the treatment of a patient.

In various embodiments, a magnetic resonance imaging guided ultrasound therapy system is disclosed performing an imaging method as described herein. The system can be used for ultrasonic tissue ablation.

Features of the disclosed embodiments may be combined, rearranged, omitted, etc., within the scope of the invention to produce additional embodiments. Furthermore, certain features may sometimes be used to advantage without a corresponding use of other features.

It is, thus, apparent that there is provided, in accordance with the present disclosure, medical imaging contrast devices, methods, and systems. Many alternatives, modifications, and variations are enabled by the present disclosure. While specific embodiments have been shown and described in detail to illustrate the application of the principles of the invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A method of controlling an imaging signal through microbubble fragmentation, comprising:
    fabricating and storing microbubbles at a first time, and at a later time, recovering pre-fabricated microbubbles;
    introducing pre-fabricated microbubbles into a portion of a host;
    bursting the microbubbles using an external acoustic force; and
    imaging the portion of the host using an imaging device;
    the microbubbles being configured to include a paramagnetic inhomogeneity at a gas-liquid interface when intact, and are further configured such that the paramagnetic inhomogeneity disappears after the bursting of the microbubbles, and
    controlling the imaging signal responsively to a state of the microbubbles, the state of the microbubbles being one of an intact and a fragmented state.

2. The method of claim 1, wherein the imaging includes changing, using a controller, an imaging signal from a negative contrast to a positive contrast responsively to a time of microbubble fragmentation and generating at least one image responsively to at least one of a difference in magnitude of the negative and positive contrast and a rate of change from negative to positive contrast.

3. The method of claim 1, wherein the imaging includes controlling an imaging signal intensity responsively to a concentration of the fragmented microbubbles.

4. The method of claim 3, wherein the imaging includes controlling the imaging signal such that the imaging signal intensity increases with an increase of the concentration of the fragmented microbubbles.

5. The method of claim 3, wherein the controlling is performed responsively to a concentration of a paramagnetic lanthanide bound to a fragmented microbubble membrane.

6. The method of claim 1, wherein the imaging signal includes a magnetic resonance imaging signal and the imaging device includes one of a magnetic resonance imaging device and an ultrasound imaging device.

7. The method of claim 1, wherein the microbubbles include a membrane enveloping a fluid, the paramagnetic inhomogeneity being generated by a paramagnetic lanthanide bound to a surface of the membrane.

8. The method of claim 7, wherein the paramagnetic lanthanide is bound to the surface of the membrane by post-labeling.

9. The method of claim 7, wherein the membrane includes a lipid coating and the paramagnetic lanthanide is bound to the lipid coated membrane by post-labeling.

10. The method of claim 9, wherein the post-labeling includes:
    functionalizing the membrane with a macrocyclic ligand; and
    loading the paramagnetic lanthanide through chelation to the macrocyclic ligand which is conjugated to the membrane.

11. The method of claim 10, wherein the macrocyclic ligand includes a metal chelating ligand.

12. The method of claim 11, wherein the metal chelating ligand includes one of a 1,4,7,10-Tetraazacyclododecane-1,4,7,10-tetraacetic acid (DOTA), a 1,4,7,10-Tetraazacyclododecane-1,4,7,10-tetraacetic acid monoacid mono(N-hydroxysuccinimide ester) (DOTA-NHS), or a (DTPA).

13. The method of claim 10, wherein the lipid coated membrane includes 1,2-distearoyl-sn-glycero-3-phosphoethanolamine (DSPE).

14. The method of claim 10, further comprising reacting the macrocyclic ligand with a primary amino group on the lipid coated membrane.

15. The method of claim 7, wherein the paramagnetic lanthanide includes gadolinium $Gd^{3+}$.

16. The method of claim 1, wherein the controlling of the image signal includes spatial and temporal control.

17. A method of real-time monitoring of location, intensity and dose of ultrasound energy deposition in a tissue, comprising:
    introducing pre-fabricated microbubbles into a portion of a host;
    bursting the microbubbles using ultrasound; and
    imaging the portion of the host using an imaging device, the imaging including visualizing an ultrasound-induced microbubble destruction on an image generated using magnetic resonance imaging, the microbubbles including a fluid core, a membrane enveloping the fluid core, and a material bound to the membrane which is capable of creating a magnetic inhomogeneity at gas-liquid interfaces of the microbubbles, the pre-fabricated microbubbles being configured such that the magnetic inhomogeneity disappears after the bursting of the microbubbles,
    wherein the image changes from a negative to a positive image contrast based on a concentration of material remaining on fragmented microbubble membranes.

18. A method of producing an image, comprising:
    creating a magnetic inhomogeneity at gas-liquid interfaces of size-selected lipid-coated microbubbles by post-labeling;
    introducing the microbubbles into a portion of a host;

bursting the microbubbles using ultrasound to thereby open a blood-brain-barrier (BBB) in the blood capillary endothelium of the host; and imaging the blood-brain-barrier opening using an electromagnetic scanner, the imaging including visualizing ultrasound-induced microbubble destruction on an image generated using the electromagnetic scanner, wherein the image changes from a negative to a positive image contrast based on a concentration of material remaining on fragmented microbubble membranes.

19. A system for producing an image, comprising:

a microbubble generator to generate lipid-coated microbubbles including a membrane enveloping a fluid and a material bound to the membrane, the material being capable of creating a magnetic inhomogeneity at gas-liquid interfaces of the microbubbles;

an ultrasound device to burst the microbubbles after insertion of the lipid-coated microbubbles into a host; and an imaging device to image a portion of the host after insertion of the lipid-coated microbubbles into the host;

the imaging device being further configured to allow for visualizing ultrasound-induced microbubble destruction, wherein the image changes from a negative to a positive image contrast based on a concentration of the material remaining on fragmented microbubble membranes.

20. A method of preparing and using a plurality of paramagnetic material-bound lipid microbubbles, comprising:

preparing a plurality of microbubbles, each microbubble including a lipid coated membrane encapsulating a fluid;

inserting the lipid-coated microbubbles into a holding device;

separating the microbubbles having a size within a predetermined size range from the rest of the microbubbles by applying centrifugation on the holding device, collecting the microbubbles having a size within the predetermined range into a solid concentrate at an upper side of the holding device;

removing the microbubbles that are not in the solid concentrate from the holding device, so as to allow the separated microbubbles to be stored and transported in the holding device;

labeling the separated microbubbles with a paramagnetic material prior to using the microbubbles, wherein the labeling includes:

functionalizing the membranes of the separated microbubbles with a macrocyclic ligand; and loading the paramagnetic material through chelation to the macrocyclic ligand which is conjugated to the membranes;

inserting the plurality of paramagnetic material-bound lipid microbubbles into a host;

bursting the inserted microbubbles using ultrasound; and controlling an imaging signal responsively to a state of the microbubbles, the state of the microbubbles being characterizable as one of intact and fragmented.

21. A method of monitoring a location, intensity and/or dose of ultrasound energy deposition in a tissue, comprising:

introducing pre-fabricated microbubbles into a portion of a host;

bursting the microbubbles using ultrasound; and imaging the portion of the host using an imaging device, the imaging including visualizing an ultrasound-induced microbubble destruction on an image generated using magnetic resonance imaging, the microbubbles including a membrane and a material bound to the membrane which is capable of creating a magnetic inhomogeneity at gas-liquid interfaces of the microbubbles, the microbubbles being configured such that the magnetic inhomogeneity disappears after the bursting of the microbubbles, wherein the image changes from a negative to a positive image contrast based on a concentration of the material remaining on fragmented microbubble membranes, and wherein the imaging includes changing, using a controller, the imaging signal from the negative contrast to the positive contrast responsively to a time of microbubble fragmentation and generating at least one image responsively to at least one of a difference in magnitude of the negative and positive contrast and a rate of change from negative to positive contrast.

* * * * *